US006447811B1

(12) United States Patent
Ravensberg et al.

(10) Patent No.: US 6,447,811 B1
(45) Date of Patent: Sep. 10, 2002

(54) PESTICIDE AGAINST PLANT-PATHOGENIC MICROORGANISMS

(75) Inventors: Willem Jacobus Ravensberg, Zoetermeer; Richard Karel Van der Pas, Rotterdam; Klaas Daniel Kussendrager, Veghel; Johannes Antonius Maria Maas, Gemert, all of (NL)

(73) Assignees: Koppert B.V. (NL); Campina-Melkunie B.V. (NL)

( * ) Notice: Subject to any disclaimer, the term of this patent is extended or adjusted under 35 U.S.C. 154(b) by 0 days.

(21) Appl. No.: 09/530,728

(22) PCT Filed: Nov. 5, 1998

(86) PCT No.: PCT/NL98/00640

§ 371 (c)(1),
(2), (4) Date: Jun. 30, 2000

(87) PCT Pub. No.: WO99/22597

PCT Pub. Date: May 14, 1999

(30) Foreign Application Priority Data

Nov. 5, 1997 (NL) ............................................. 1007457

(51) Int. Cl.⁷ ........................ A01N 63/00; A01N 59/12; A01N 59/00; A01N 47/48; A61K 38/54

(52) U.S. Cl. ..................... 424/670; 424/94.2; 424/94.4; 424/94.61; 424/616; 424/667; 424/669; 424/671; 514/23; 514/460; 514/514; 514/515; 514/547; 514/772; 514/777; 514/778; 514/779; 514/780; 514/781; 514/782; 514/783; 514/785; 514/786; 504/150; 504/151; 504/154

(58) Field of Search ................................ 424/94.2, 94.3, 424/669–671, 195.1, 616, 94.4, 94.61, 667; 514/514, 515, 23, 460, 547, 772, 777–783, 785–786; 504/150, 151, 154

(56) References Cited

FOREIGN PATENT DOCUMENTS

| WO | 91/11105 | * 8/1991 |
| WO | WO9726908 | 7/1997 |

OTHER PUBLICATIONS

Research Disclosure, No. 333, XP 000281314, "Anti–Microbial Compositions," p. 92, 1/1992.*

N. V. Rama Raje Urs et al., "Bactericidal Activity of Horseradish Peroxidase on *Xanthomonas phaseoli* var. sojensis", Apr. 1974, pp. 542–545.

* cited by examiner

*Primary Examiner*—John Pak
(74) *Attorney, Agent, or Firm*—Webb Ziesenheim Logsdon Orkin & Hanson, P.C.

(57) ABSTRACT

A formulation comprising lactoperoxidase, thiocyanate and/or iodide and a hydrogen peroxide donor system, in particular glucose oxidase and glucose, is useful for controlling plant-pathogenic microorganisms such as fungi and bacteria. Preferably the formulation also contains an oil.

47 Claims, No Drawings

PESTICIDE AGAINST PLANT-PATHOGENIC MICROORGANISMS

This application is a 371 of PCT/NL98/00640, filed on Nov. 5, 1998.

The present invention relates to a composition for controlling pathogenic bacteria and/or fungi on plants, trees and the like, in addition to a method wherein the composition is applied.

There exist different types of pesticides against organisms such as bacteria and fungi. These are often synthetic agents with possible drawbacks for humans, animals and environment. These agents moreover often have the drawback that the organism for controlling becomes resistant to the agent. A new agent must then be found for controlling the relevant pathogen.

It is further known of some fungicides that their activity is linked to temperature or that their activity depends on a determined degree of humidity. For treating plants and trees, which grow in the open air, such limited conditions of use are a great drawback. But similar problems can also occur in the case of crops cultivated in greenhouses.

The object of the present invention is therefore to provide a new pesticide which does not have the above stated drawbacks and which can be used to control pathogenic bacteria and fungi on plants, trees and the bike in situ.

This object is achieved according to the invention with a composition comprising lactoperoxidase, thiocyanate ($SCN^-$) and/or iodide ($I^-$) and a hydrogen peroxide donor system, in particular glucose oxidase and glucose. In addition to the glucose oxidase/glucose system other hydrogen donor systems can also be used such as sodium percarbonate or stabilized hydrogen peroxide.

An advantage of this new agent according to the invention is that the danger of resistances is very small or even absent. Moreover it is an agent on a natural basis.

The antimicrobial activity of lactoperoxidase is per se known and described for instance in European patent no. 0 514 417 and international application WO97/26908. These relate however to application of this so-called LP system (lactoperoxidase system) for conserving cosmetic products or for medical purposes in humans and animals. Because the treatment of microbial infections in plants, trees and parts thereof takes place under entirely different (and often greatly varying) conditions than in humans and animals, it is not obvious that known systems based on lactoperoxidase could also have an in situ biocidal effect on plant pathogens.

As already indicated above, many plants, particularly agricultural crops, and trees grow in the open air and are thereby subjected to weather conditions such as wind, rain, sunshine, changing temperatures and the like. All these factors can reduce the effectiveness of a system which is based on enzymes, which are after all relatively sensitive as compared to chemical pesticides. A skilled person in the field of pesticides will hereby not immediately appreciate the usefulness and wide applicability of a pesticide based on lactoperoxidase.

In a preferred embodiment of the present invention an oil base is also added to the composition. By including a relatively small quantity of an oil base in the composition the effectiveness of the composition is further improved in surprising manner.

The oil has the object of ensuring a good distribution of the composition on the leaves and other parts of the plant and of preventing evaporation of the agent, which is in fact an aqueous composition. The activity of the composition does not depend on a specific temperature or relative humidity. The chance of resistance to the composition being developed is small, because the system has no specific effect on micro-organisms, such as antibiotics do have. Plants, animal and human cells are insensitive to the system.

The composition according to the invention comprises for instance per liter of aqueous solution at least 10 mg lactoperoxidase; at least 50 I.E. glucose oxidase; at least 0.05% glucose; at least 25 mg iodide ($I^-$), at least 5 mg thiocyanate ($SCN^-$); and optionally a maximum of 1 v/v % oil base. A maximum of 0.2 v/v % spreading agent can optionally further be present. The composition preferably comprises per liter of aqueous solution at least 50 mg lactoperoxidase; at least 100 I.E. glucose oxidase; at least 0.1 w/v % glucose; at least 50 mg iodide ($I^-$); at least 10 mg thiocyanate ($SCN^-$) and optionally a maximum of 0.1 v/v % oil base. A maximum of 0. 1% spreading agent can optionally further be present.

A good activity of the composition is obtained when it comprises per liter of aqueous solution 10–100 mg, preferably 30–70 mg lactoperoxidase; 50–1000 I.E., preferably 100–250 I.E. glucose oxidase; 0.05–2 w/v %, preferably 0.1–1 w/v % glucose; 25–200 mg, preferably 50–100 mg iodide ($I^-$); 5–50 mg, preferably 10–20 mg thiocyanate ($SCN^-$) and optionally 0.1–2 v/v %, preferably 0.2–1 v/v % oil base. The quantity of spreading agent which may optionally be added amounts to 0.01–0.2 v/v %, preferably 0.05–0.07 v/v %.

The oil base always consists of at least an oil and an agent for emulsifying the oil in the aqueous solution to form an oil-in-water emulsion. This agent for emulsifying can be a separate emulsifier but can also be formed by the oil itself, which has self-emulsifying properties. Such self-emulsifying oils can be manufactured by modifying oil, for instance by ethoxylating. On the basis of his professional knowledge the skilled person can select the most suitable emulsifier for a determined oil.

The oil used in the oil base is chosen from the group of mineral oils, vegetable oils, animal oils or is a mixture of one or more oils from one or more of these groups. Recommended are oils which inherently already have a greater or lesser degree of antimicrobial activity.

Examples of vegetable oils are peanut oil, sesame oil, rape-seed oil, linseed oil, castor oil, soybean oil, corn germ oil, cotton-seed oil. Of these peanut oil is found to be particularly suitable for the purpose of the invention.

In the case of an animal oil, for instance fish oil such as herring oil or mackerel oil is chosen. Suitable mineral oils are for instance diverse types of paraffin oil or kerosine-type oils.

In order to further facilitate the distribution of the composition over the surface for treating, one or more spreading agents can further be added to the composition or the oil base. A skilled person in this field is very well capable of selecting suitable spreading agents. Such spreading agents are usually non-ionogenic surface tension-reducing substances. Recommended are ethoxylated alcohols, for instance Volpo T7™, and phosphatidyl lipids, such as Nathin 130™.

In a particularly suitable embodiment of the composition according to the invention, the oil base consists of at least 80–90, preferably 85 parts oil; 5–15, preferably 10 parts emulsifier; optionally 1–10, preferably 5 parts of a lecithin fraction. Optionally 0.01–0.2 v/v %, preferably 0.05 v/v % spreading agent can be added to the composition per liter of aqueous solution.

In a preferred embodiment the composition according to the invention comprises an oil base consisting of peanut oil, a polyoxyethylene sorbitol hexaoleate, such as the emulsifier Atlas 1086™ (ICI) and a lecithin fraction consisting of phosphatidyl lipids, such as Nathin 130™ (ENR), in addition to a spreading agent consisting of ethoxylated alcohols, such as Volpo T7™ (CRODA).

In order to prolong the activity of the composition in situ, one or more adhesives can be added. Adhesives ensure for instance that the constituents of the composition are not rinsed off the plant by rain or other conditions. Adhesives can also be selected in simple manner by a skilled person in this field from the available supply. Examples are starch, gums such as xanthan gum, gum Arabic and carboxymethyl celluloses (CMCs).

The composition can be applied by means of spraying, sprinkling, atomizing, overhead spraying, watering, immersing, drip irrigation. A particularly advantageous method for applying the composition is spraying both by means of low volume methods (mist systems) and high volume methods. Drip irrigation can be used for culture systems on rockwool and other growth substrates. The agent according to the invention can also be used to disinfect drip irrigation systems. In both latter cases the presence of the oil base is not strictly necessary for an optimal activity. Immersion in a bath with the composition is particularly suitable for the treatment of plant parts, in particular harvestable parts, such as bulbs, tubers, fruits and the like.

The composition according to the invention can be made commercially available in different forms. A form is recommended wherein the activity of the enzyme lactoperoxidase is delayed as long as possible because this increases the shelf-life of the product. The activity of the enzyme lactoperoxidase starts as soon as a hydrogen peroxide donor is present. In the present case the glucose oxidase/glucose system is the hydrogen peroxide donor. It is therefore recommended, at least for determined applications, to supply the hydrogen peroxide donor separately of the enzyme lactoperoxidase. In addition, the oil base and the spreading agent can, if desired, also be packaged separately.

In a particular embodiment of the invention a kit is therefore provided for forming the composition, which kit comprises an optionally concentrated enzyme composition consisting of at least lactoperoxidase and optional additives, a hydrogen peroxide donor composition consisting of at least glucose oxidase and glucose, thiocyanate and/or iodide and optional other additives, and an oil composition consisting of at least oil, an optional emulsifier, optional spreading agents and optional other additives, wherein the three compositions must be mixed with each other before use in a ratio such that a composition according to the invention is obtained.

The composition according to the invention can optionally be marketed in a concentrated form which may or may not be dry. The final composition is then obtained by dilution or dissolving in for instance water.

Fungi which can be successfully controlled with the composition according to the invention are inter alia: Botryotinia spp ("grey moulds"), such as for instance *B. fuckeliana* (anamorphic *Botrytis cinerea*), Didymella spp, such as for instance *D. bryonia* (=Mycospherella in cucurbitaceae), *D. lycopersici* (=cancer in tomato), Puccunia spp ("rusts"), such as for instance *P. horiana* (=Japanese rust), Sphaerotheca spp ("true mildew"), such as for instance *S. fuliginea* (mildew in cucumber) and *S. pannose* (mildew in rose), Erysiphe spp, Oidium spp and *Leveillula taurica* (also true mildew types), Fusarium spp ("foot rot and/or wilt disease"), Phytophtora spp ("foot and/or root disease"), Pythium spp ("foot disease"), Plasmopara, Peronospora, and Sclerospora spp (the downy mildew types), Rhizoctonia, Verticillium and Sclerotinia spp (causes of spot), Rhizopus and Penicillium spp (causes of (storage)rot) and Venturia spp (causes of scab).

Bacterial infections which can be treated with the composition according to the invention are inter alia infections by *Erwinia chrysanthemi, Pseudomonas syringae, Xanthomonas campestris, Curtobactrium flaccumfaciens.*

The composition and the method according to the invention can be used in the broadest sense for plant protection and pathogen control in for instance agriculture, horticulture, vegetable growing, ornamental plant cultivation, fruit growing, bulb growing, the culture of potted plants, forestry etc., and as consumer product for indoor plants. In addition to the plants and trees themselves, plant parts can also be treated such as bulbs, tubers, flowers, cuttings, fruits and the like.

Plant protection and pathogen control are understood to mean according to the invention both preventive and curative activities. In most cases however this will relate to the killing of pathogens which are already present. In a number of other cases however, preventive treatment of plant parts can also be envisaged. The composition according to the invention requires free water to be active, but can be made active again after being dried by adding water.

The composition according to the invention is a natural pesticide and therefore environmentally-friendly.

The invention further relates to a method for controlling plant-pathogenic bacteria and/or fungi on plants, trees and parts thereof, comprising of applying the composition according to the invention to the plant, tree or part thereof.

The invention will be further elucidated with reference to the following examples, which are only given by way of illustration.

EXAMPLES

Example 1

Direct Activity of the Agent According to the Invention Against *Verticillium lecanii*

Use is made of a spore powder of the fungus *Verticillium lecanii*, which is used as test organism, at a concentration of about $10\times10^{10}$ spores/gram. 10 grams is weighed off and suspended in 100 ml water. The spores must then be left to steep for a minimum of half an hour.

500 mL of the agent of the invention is made with the ingredients stated in Table 1.

TABLE 1

| | Quantity/500 ml: |
|---|---|
| lactoperoxidase (LP) | 35 mg (1 mg = 1000 ABTS U*) |
| glucose oxidase (GO) | 12.5 mg (250 u/l**) |
| potassium iodide (KI) | 65 mg (100 ppm $I^-$) |
| potassium cyanate (KSCN) | 16.5 mg (20 ppm $SCN^-$) |
| Glucose | 1.25 g (0.25 w/v %) |
| oil-base | 1.3 ml (1:375 v/v) |
| spreading agent | 0.25 ml (0.05 v/v %) |
| Water | supplement to 500 ml |

*1 Unit LP: is the quantity of lactoperoxidase per ml which gives an extinction increase of 4.41 per minute at 412 nm in a substrate solution of 1 mM ABTS and 0.1 mM hydrogen peroxide in 50 mM citrate buffer at a pH of 5.0 and a temperature of 37° C. (ABTS = 2,2 azino-di-(3-ethylbenzothiazoline)-6-sulphonate)
**1 Unit GO The quantity of enzyme which can oxidize 30 mg/l glucose in 15 minutes at 35° C. and pH 5.1.

The aqueous solution is adjusted to pH 6.5 with citric acid. 10 ml spore suspension is then added to 90 ml agent.

The lactoperoxidase system is subsequently given 1, 3, 5 and 15 minutes to act on the spores and at each point in time 1 ml is taken out and diluted 1000× with tap water to dilute the lactoperoxidase system.

30 μl is removed from this diluted solution and pipetted onto a SDA (Sabouraud Dextrose Agar) plate. After 24 and 48 hours the percentage of germinating spores is determined.

This percentage is compared with a blank. The blank contains 10 ml spore suspension with 90 ml water which is also diluted 1000× and a droplet of 30 μl of which is placed on SDA. The experiment is performed at a temperature of 21° C.

It was found that *Verticillium lecanii* was killed off in this manner to an extent of 99% by the agent according to the invention within 1 minute.

Example 2

Activity on *Verticillium lecanii* after the Agent has been Active for 24 Hours The experiment is performed as described in example 1 with the difference that the lactoperoxidase system is first stored for 24 hours in the 500 ml retort, only after which the spore suspension is added. This has the purpose of seeing whether the system is still active after 24 hours.

With this formulation and after the system has been active for 24 hours *Verticillium lectanii* is still killed off to an extent of than 99% within 1 minute.

Example 3

Activity of the Agent without I⁻ Against *Verticillium lecanii*

The experiment is performed as described in example 1 with an agent in which no KI (I⁻) is present. Only the activity on the spores immediately after starting the enzyme system was examined here.

*Verticillium lecanii* was killed off to an extent of only 25% by this composition and embodiment. This shows that addition of I⁻ significantly increases the biocidal activity on fungi.

Example 4

Activity of the Agent Against *Verticillium lecanii* Without SCN⁻

The experiment is performed as described in example 1, with the difference that no KSCN (SCN⁻) is present. The immediate activity on the spores was examined.

*Verticillium lecanii* was killed off to an extent of 99t by the agent according to the invention.

Example 5

Activity of the Agent Against *Verticillium lecanii* at Different Temperatures The experiment is performed as described in example 1 but at two different temperatures (±10° C. and 37° C.).

*Verticillium lecanii* was killed off to an extent of 99% by the agent at both temperatures within 1 minute.

Example 6

Activity of the Agent Against *Botrytis cinerea*

The experiment is performed as according to example 1 with *Botrytis cinerea* spores instead of *Verticillium lecanii* spores. After 30 and 60 minutes incubation the number of surviving spores is determined.

More than 99% of the Botrytis cinerea spores are killed off by the agent within 30 minutes.

Example 7

Direct Effect of the Agent According to the Invention Against *Sphaerotheca fuliqinea* (Cucumber Mildew)

Plastic petri dishes are used for the bioassay with a diameter of 9 cm. Each petri dish is filled with a layer of 8 to 10 mm agar. The agar is prepared by dissolving 10 gram of agar powder in 1 liter of water and bringing this just to the boil. Hereafter the agar is decanted into a beaker and placed in a cold water bath. When the agar solution has cooled to about 50° C. the petri dishes are filled. Just before solidifying (at temperature 30–40° C.), round cucumber leaf punches are arranged on the agar. The leaf punches have the same diameter as the petri dish and are laid on the agar with the underside of the leaf facing downward. In this manner the leaf can remain fresh for about 14 days.

The leaf punches are subsequently inoculated with *Sphaerotheca fuliginea*. A cucumber leaf with fresh mildew is rinsed with a plant spray for this purpose. The rinsing water with mildew spores therein is collected in a beaker. The bioassay dishes with the leaf punches are sprayed with this rinsing water using a Badger sprayer (2 bar). The dishes are dried in air and placed with the cover thereon in a space with a relative humidity (RH) of 75%. An RH of 75% is obtained by dissolving 150 gram NaCl in 100 ml water. The NaCl solution is placed in a closed container with gauze over the liquid on which the bioassay dishes can lie.

One to two days after inoculation of the leaf punches with the mildew the bioassay dishes are sprayed with diverse variations of the agent according to the invention. Water and a chemical spraying are included as references.

The bioassay dishes are sprayed with a Badger sprayer (2 bar) and dried in air. The closed petri dishes are placed above a saturated salt solution with an RH of 75%.

Six to seven days after inoculation of the mildew the bioassay dishes are assessed for the appearance of mildew and the percentage of leaf covering of the mildew. If necessary, and possible, the leaf punches are sprayed again with the agent according to the invention 7 days after inoculation of the mildew. Five days after the second spraying the leaf punches are assessed again.

500 ml of agent are made with the ingredients in Table 2.

TABLE 2

| | Quantity/500 ml: |
|---|---|
| Lactoperoxidase (LP) | 15 mg (1 mg = 1000 ABTS U*) |
| glucose oxidase (GO) | 25 mg (500 u/l**) |
| potassium iodide (KI) | 32.5 mg (50 ppm I⁻) |
| potassium cyanate (KSCN) | 8.25 mg (10 ppm SCN⁻) |
| Glucose | 5.0 g (1.0 w/v %) |
| Water | Supplement to 500 ml |

*1 Unit LP: is the quantity of lactoperoxidase per ml which gives an extinction increase of 4.41 per minute at 412 nm in a substrate solution of 1 mM ABTS and 0.1 mM hydrogen peroxide in 50 mM citrate buffer at a pH of 5.0 and a temperature of 37° C. (ABTS = 2,2 azino-di-(3-ethylbenzothiazoline)-6-sulphonate)
**1 Unit GO The quantity of enzyme which can oxidize 30 mg/l glucose in 15 minutes at 35° C. and pH 5.1.

Example 8

Activity of the Agent at Diverse Lactoperoxidase Concentrations

The experiment is performed as described in example 7, with the difference that instead of 30 mg/l lactoperoxidase a concentration of 100 mg/l lactoperoxidase (50 mg/500 ml) is used.

At these concentrations the agent gives a control result on *Sphaerotheca fuliginea* of about 55 to 65%.

Example 9

Activity of the Agent at Diverse Lactoperoxidase Concentrations and an Oil Base The experiment is performed as described in example 7, with the difference that, in addition to the components mentioned therein, an oil base consisting of peanut oil, the emulsifier Atlas 1086™ (ICI) and the spreading agents Nathin 130™+Volpo T7™ is added. This oil base is added in a concentration of 1:250.

The agent with 30 mg/l lactoperoxidase+oil base gives a control result on *Sphaerotheca fuliginea* of about 50–55% and the agent with 100 mg/l lactoperoxidase+oil base gives a control result on *Sphaerotheca fuliqinea* of about 80–95%.

The chemical reference gives a control result on *Sphaerotheca fuliginea* of about 80–95%. Water has no noticeable control result on *Sphaerotheca fuliginea*.

Example 10

Semi-field Experiment for Testing the Activity of the Agent Against *Sphaerotheca fuliginea* on Cucumber Plant 10 to 15 young cucumber plants are placed in closed cages placed in a greenhouse. The cucumber plants are unsprayed and not resistant to mildew. They are about 60 cm high and have four to five cucumber leaves. The plants are inoculated on day 1 with mildew by spraying a spore solution of mildew over the plants (see Example 7 for obtaining mildew spores). On day 7 the plants are treated with the agent according to the invention, water or a chemical control. The treatments are sprayed over the plants with a spraying lance at about 5 bar. On day 8 and the following days the plants are assessed for percentage of mildew damage. If necessary, a second spraying takes place on day 14 with the diverse agents according to the invention.

The initial damage before'spraying is 50% for the plants treated with the agent according to the invention and 50% for the plants treated with chemical control.

1000 ml of agent is made with the ingredients in Table 3.

TABLE 3

| | Quantity/liter: |
|---|---|
| lactoperoxidase (LP) | 100 mg (1 mg = 1000 ABTS U*) |
| glucose oxidase (GO) | 50 mg (500 u/l**) |
| potassium iodide (KI) | 130 mg (100 ppm I⁻) |
| potassium cyanate (KSCN) | 33 mg (20 ppm SCN⁻) |
| glucose | 10 g (1 w/v %) |

TABLE 3-continued

| | Quantity/liter: |
|---|---|
| oil formulation | 1:250 v/v |
| water | Supplement to 1000 ml |

*1 Unit LP: is the quantity of lactoperoxidase per ml which gives an extinction increase of 4.41 per minute at 412 nm in a substrate solution of 1 mM ABTS and 0.1 mM hydrogen peroxide in 50 mM citrate buffer at a pH of 5.0 and a temperature of 37° C. (ABTS = 2,2 azino-di-(3-ethylbenzothiazoline)-6-sulphonate)
**1 Unit GO The quantity of enzyme which can oxidize 30 mg/l glucose in 15 minutes at 35° C. and pH 5.1.

At this concentration the agent gives a control result on *Sphaerotheca fuliginea* of about 80%.

The chemical control gives a control result on *Sphaerotheca fuliginea* of about 40%.

Example 11

Semi-field Experiment for Testing the Activity of the Agent Against *Sphaerotheca fuliginea* on Cucumber Plant with Addition of Spreading Agent The experiment is performed as described in example 10, with the difference that a spreading agent is added. The concentration of the spreading agent Volpo T7™ is 0.05%. The initial damage with mildew before spraying is 35–40%.

At this concentration the agent without spreading agent gives a control result on *Sphaerotheca fuliginea* of about 85% relative to water. At this concentration the agent with the spreading agent as extra additive gives a control result on *Sphaerotheca fuliginea* of about 99%.

Example 12

Field Experiment for Testing the Activity of the Agent Against *Sphaerotheca fuliginea* on Cucumber Plant with and without Spreading Agent The method used for the field experiments is the same as the method description of semi-field experiments from example 10, with the difference that fully grown plants are used in a greenhouse and spraying is carried out with either a knapsack sprayer or a spray barrow.

1000 l of agent is made with the ingredients of Table 4.

The initial damage by *Sphaerotheca fuliginea* on cucumber plant before spraying is 80–90%. There is treatment with and without spreading agent.

TABLE 4

| | Quantity/1000 liter: |
|---|---|
| lactoperoxidase (LP) | 70 g (1 mg = 1000 ABTS U*) |
| potassium iodide (KI) | 130 g (100 ppm I) |
| potassium cyanate (KSCN) | 33 g (20 ppm SCN⁻) |
| glucose oxidase (GO) | 25 g (250 u/l**) |
| glucose | 2500 g (0.25 w/v %) |
| oil formulation | 2666 ml (1:375 v/v) |
| spreading agent | 500 ml (0.05 v/v %) |

*1 Unit LP: is the quantity of lactoperoxidase per ml which gives an extinction increase of 4.41 per minute at 412 nm in a substrate solution of 1 mM ABTS and 0.1 mM hydrogen peroxide in 50 mM citrate buffer at a pH of 5.0 and a temperature of 37° C. (ABTS = 2,2 azino-di-(3-ethylbenzothiazoline)-6-sulphonate)
**1 Unit GO The quantity of enzyme which can oxidize 30 mg/l glucose in 15 minutes at 35° C. and pH 5.1.

The agent with spreading agent gives a control result on *Sphaerotheca fuliginea* of about 90%. The agent without spreading agent gives a control result of about 75%.

Example 13

Activity of the Agent Against *Sphaerotheca fuliginea* on Cucumber Plants with Diverse Concentrations of Lactoperoxidase The experiment as performed as described in example 12, with the difference that the concentration of lactoperoxidase (LP) is varied as follows: 70 mg/l, 60 mg/l and 50 mg/l.

No difference is found in this experiment between the diverse concentrations of lactoperoxidase. The control result of all three of the LP concentrations is about 75 to 85%.

Example 14

Activity of the Agent Against *Leveillula taurica* on Paprika Plants

The experiment is performed as described in example 12 with a knapsack sprayer, with the difference that instead of cucumber paprika with the mildew associated therewith, *Leveillula taurica*, is used. No spreading agent is used.

At this concentration the agent gives a control result on mildew (*Leveillula taurica*) on paprika of about 60–70%.

Example 15

Activity of the Agent Against *Oidium lycopersicum* on Tomato Plants

The experiment is performed as described in example 12 with a knapsack sprayer, with the difference that instead of cucumber tomato with the mildew associated therewith, *Oidium lycopersicum*, is used.

At this concentration the agent according to the invention gives a control result on mildew (*Oiduim lycopersicum*) on tomato of about 80–85%.

Example 16

Activity of the Agent Against *Xanthomonas campestris*

A bacteria solution is made of about $_{10}{}^{8}$ spores/ml in Nutrient Broth. 500 ml agent is made with the ingredients of Table 5.

TABLE 5

| | Quantity/500 ml: |
|---|---|
| lactoperoxidase (LP) | 35 mg (1 mg = 1000 ABTS U*) |
| glucose oxidase (GO) | 12.5 mg (250 u/l**) |
| potassium iodide (KI) | 65 mg (100 ppm $I^-$) |
| potassium cyanate (KSCN) | 16.5 mg (20 ppm $SCN^-$) |
| glucose | 1.25 g (0.25%) |
| nutrient Broth | supplement to 500 ml |

*1 Unit LP: is the quantity of lactoperoxidase per ml which gives an extinction increase of 4.41 per minute at 412 nm in a substrate solution of 1 mM ABTS and 0.1 mM hydrogen peroxide in 50 mM citrate buffer at a pH of 5.0 and a temperature of 37° C. (ABTS = 2,2 azino-di-(3-ethylbenzothiazoline)-6-sulphonate)
**1 Unit GO: The quantity of enzyme which can oxidize 30 mg/l glucose in 15 minutes at 35° C. and pH 5.1

10 ml bacteria suspension is added to 90 ml of the agent. The agent is then given 5, 10, 15 and 30 minutes to act on the bacteria and at each point in time 1 ml is taken out and diluted 1000× in Nutrient Broth in order to dilute the agent.

From this diluted solution 0.1 ml is removed and pipetted onto a NUA (Nutrient Agar) plate and plated out. After 72 hours the plates are assessed for bacterial growth. This is compared with a blank.

The experiment is performed at a temperature of 21° C. and at a pH of about 7.5.

Use is made in this experiment of the bacteria *Xanthomonas campestris.*

In this manner *Xanthomonas campestris* is killed to an extent of 100% within 5 minutes by the agent according to the invention.

Example 17

Activity of the Agent Against *Pseudomonas syringae*

The experiment is performed as described in example 16, with the difference that the bacteria *Pseudomonas syringae* was tested instead of *Xanthomonas campestris.*

*Pseudomonas syringae* was killed to an extent of 100% within 5 minutes by this formulation and in this manner.

What is claimed is:

1. A composition for the control of plant-pathogenic organisms comprising lactoperoxidase, thiocyanate ($SCN^-$) and/or iodide ($I^-$), a hydrogen peroxide donor system, an oil base, and a spreading agent selected from the group consisting of phosphatidyl lipids and ethoxylated alcohols, wherein the components of the composition are present in amounts effective to control plant pathogen organisms on plants or plant parts.

2. The composition as claimed in claim 1, wherein the composition comprises per liter of aqueous solution:

at least 10 mg lactoperoxidase;

at least 50 I.U. glucose oxidase;

at least 0.05 w/v % glucose;

at least 25 mg iodide ($I^-$);

at least 5 mg thiocyanate ($SCN^-$); and a maximum of 1 v/v % of the oil base.

3. The composition as claimed in claim 1, wherein the composition comprises per liter of aqueous solution:

at least 50 mg lactoperoxidase;

at least 100 I.U. glucose oxidase;

at least 0.1 w/v % glucose;

at least 50 mg iodide ($I^-$)

at least 10 mg thiocyanate ($SCN^-$); and a maximum of 0.4 v/v % of the oil base.

4. The composition as claimed in claim 1, wherein the composition comprises per liter of aqueous solution:

10–100 mg lactoperoxidase;

50–1000 I.U. glucose;

0.05–2 w/v % glucose;

25–200 mg iodide ($I^-$)

5–50 mg thiocyanate ($SCN^-$); and 0.01–2 v/v % oil base.

5. The composition as claimed in claim 4, wherein lactoperoxidase is present in the amount of 30 mg to 70 mg per liter of aqueous solution.

6. The composition as claimed in claim 4, wherein glucose oxidase is present in the amount of 100–250 I.U. per liter of aqueous solution.

7. The composition as claimed in claim 4, wherein glucose is present in the amount of 0.1–1 w/v % per volume of aqueous solution.

8. The composition as claimed in claim 4, wherein iodide ($I^-$) is present in the amount of 50–1 00 mg per liter of aqueous solution.

9. The composition as claimed in claim 4, wherein thiocyanate (SCN⁻) is present in the amount of 10–20 mg per liter of aqueous solution.

10. The composition as claimed in claim 4, wherein the oil base is present in the amount of 0.2–1 v/v % per volume of aqueous solution.

11. The composition as claimed in claim 1, wherein the oil base comprises an oil and an agent for emulsifying the oil in the aqueous solution to form an oil-in-water emulsion.

12. The composition as claimed in claim 11, wherein the agent for emulsifying the oil in the aqueous solution consists of the oil itself, which has self-emulsifying properties.

13. The composition as claimed in claim 11, wherein the oil is chosen from the group consisting of mineral oils, vegetable oils and animal oils.

14. The composition as claimed in claim 13, wherein the vegetable oil is chosen from the group consisting of peanut oil, sesame oil, rape-seed oil, linseed oil, castor oil, soybean oil, corn germ oil and cotton-seed oil.

15. The composition as claimed in claim 13, wherein the animal oil is a fish oil chosen from the group consisting of herring oil and mackerel oil.

16. The composition as claimed in claim 13, wherein the mineral oil is chosen from the group consisting of paraffin oils and kerosine oils.

17. The composition as claimed in claim 1, wherein the concentration of the spreading agent amounts to 0.01 w/v %–0.2 w/v % per 1 liter of aqueous solution.

18. The composition as claimed in claim 1, wherein the oil base comprises:
   80–90 parts oil;
   5–15 parts emulsifier;
   1–10 parts of a lecithin fraction.

19. The composition as claimed in claim 18, wherein the oil is peanut oil, the emulsifier is polyoxyethylene sorbitol hexaoleate, the lecithin fraction is phosphatidyl lipids and the spreading agent is ethoxylated alcohols.

20. The composition as claimed in claim 1, wherein the composition further comprises one or more adhesives.

21. The composition as claimed in claim 20, wherein the adhesive is chosen from the group consisting of starch, gums, gum Arabic, and carboxymethyl celluloses (CMCs).

22. The composition as claimed in claim 1, comprising per liter of aqueous solution:
   70 mg lactoperoxidase;
   250 I.U. glucose oxidase;
   0.25 w/v % glucose;
   100 mg iodide (I⁻);
   20 mg thiocyanate (SCN⁻); and
   0.4 v/v % of an oil base consisting of:
      85 parts peanut oil;
      10 parts polyoxyethylene sorbitol hexaoleate; and
      5 parts phosphatidyl lipids.

23. A method for controlling plant-pathogenic bacteria and fungi on plants, trees and parts thereof, comprising of applying to the plant, tree or part thereof a composition as defined in claim 1, in an amount effective to control plant pathogens in plants.

24. The method as claimed in claim 23, wherein the composition is applied by means selected from the group consisting of spraying, sprinkling, atomizing, overhead spraying, watering, immersing, and drip irrigation.

25. The method as claimed in claim 23, wherein the hydrogen peroxide donor system of the compositions comprises glucose oxidase and glucose.

26. The method as claimed in claim 23, wherein the composition comprises per liter of aqueous solution:
   at least 10 mg lactoperoxidase;
   at least 50 I.U. glucose oxidase;
   at least 0.05 w/v % glucose;
   at least 25 mg iodide (I⁻);
   at least 5 mg thiocyanate (SCN⁻); and
   a maximum of 1 v/v % of the oil base.

27. The method as claimed in claim 23, wherein the composition comprises per liter of aqueous solution:
   at least 50 mg lactoperoxidase;
   at least 100 I.U. glucose oxidase;
   at least 0.1 w/v % glucose;
   at least 50 mg iodide (I⁻);
   at least 10 mg thiocyanate (SCN⁻); and
   a maximum of 0.4 v/v % of the oil base.

28. The method as claimed in claim 23, wherein the composition comprises per liter of aqueous solution:
   10–100 mg lactoperoxidase;
   50–1000 I.U. glucose oxidase;
   0.05–2 w/v % glucose;
   25–200 mg iodide (I⁻);
   5–50 mg thiocyanate (SCN⁻); and
   0.01–2 v/v % oil base.

29. The method as claimed in claim 28, wherein lactoperoxidase is present in the amount of 30 mg to 70 mg per liter of aqueous solution.

30. The method as claimed in claim 28, wherein glucose oxidase is present in the amount of 100–250 I.U. per liter of aqueous solution.

31. The method as claimed in claim 28, wherein glucose is present in the amount of 0.1–1 w/v % per volume of aqueous solution.

32. The method as claimed in claim 28, wherein iodide (I⁻) is present in the amount of 50–100 mg per liter of aqueous solution.

33. The method as claimed in claim 28, wherein thiocyanate (SCN⁻) is present in the amount of 10–20 mg per liter of aqueous solution.

34. The method as claimed in claim 28, wherein the oil base is present in the amount of 0.2–1 v/v % per volume of aqueous solution.

35. The method as claimed in claim 23, wherein the oil base of the composition comprises an oil and an agent for emulsifying the oil in the aqueous solution to form an oil-in-water emulsion.

36. The method as claimed in claim 23, wherein the agent for emulsifying the oil in the aqueous solution consists of the oil itself, which has self-emulsifying properties.

37. The method as claimed in claim 35, wherein the oil is chosen from the group consisting of mineral oils, vegetable oils and animal oils.

38. The method as claimed in claim 37, wherein the vegetable oil is chosen from the group consisting of peanut oil, sesame oil, rape-seed oil, linseed oil, castor oil, soybean oil, corn germ oil and cotton-seed oil.

39. The method as claimed in claim 37, wherein the animal oil is a fish oil chosen from the group consisting of herring oil and mackerel oil.

40. The method as claimed in claim 37, wherein the mineral oil is chosen from the group consisting of paraffin oils and kerosine oils.

41. The method as claimed in claim 23, wherein the concentration of the spreading agent amounts to 0.01 w/v % –0.2 w/v % per 1 liter of aqueous solution.

42. The method as claimed in claim 23, wherein the oil base comprises:

80–90 parts oil;

5–15 parts emulsifier;

1–10 parts of a lecithin fraction.

43. The method as claimed in claim 42, wherein the oil is peanut oil, the emulsifier is polyoxyethylene sorbitol hexaoleate, the lecithin fraction is phosphatidyl lipids and the spreading agent is ethoxylated alcohols.

44. The method as claimed in claim 23, wherein the composition further comprises one or more adhesives.

45. The method as claimed in claim 44, wherein the adhesive is chosen from the group consisting of starch, gums, gum Arabic, and carboxymethyl celluloses (CMCs).

46. The method as claimed in claim 23, wherein the composition comprises per liter of aqueous solution;

70 mg lactoperoxidase;

250 I.U. glucose oxidase;

0.25 w/v % glucose;

100 mg iodide ($I^-$);

20 mg thiocyanate ($SCN^-$); and 0.4 v/v % of an oil consisting of:

85 parts peanut oil;

10 parts polyoxyethylene sorbitol hexaoleate, and 5 parts phosphatidyl lipids.

47. A kit for forming a composition as defined in claim 1, comprising an optionally concentrated enzyme composition comprising lactoperoxidase, a hydrogen peroxide donor composition containing thiocyanate and/or iodide, an oil base composition and a spreading agent selected from the group consisting of phosphatidyl lipids and ethoxylated alcohols, wherein the enzyme composition, hydrogen peroxide donor composition, oil base composition and spreading agent must be mixed with each other before use in a ratio so that a composition according to claim 1 is obtained.

* * * * *

UNITED STATES PATENT AND TRADEMARK OFFICE
CERTIFICATE OF CORRECTION

PATENT NO. : 6,447,811 B1
DATED : September 10, 2002
INVENTOR(S) : Willem Jacobus Ravensberg et al.

It is certified that error appears in the above-identified patent and that said Letters Patent is hereby corrected as shown below:

Column 1,
Line 26, "bike" should read -- like --.

Column 5,
Lines 28-29, "extent of than" should read -- extent of more than --.
Line 51, "99t by" should read -- 99% by --.

Column 7,
Line 1, before EXAMPLE 8 insert -- At these concentrations the agent gives a control result on *Sphaerotheca fuliginea* of about 20 to 25% --.

Column 9,
Line 26, "*Oidium*" should read -- *Oiduim* --.
Line 31, "*Oidium*" should read -- *Oiduim* --.
Line 40, "about $_{10}{}^8$" should read -- about $10^8$ --.

Column 10,
Line 44, "(I⁻)" should read -- (I⁻); --.
Line 50, "glucose;" should read -- glucose oxidase; --.
Line 66, "50-1 00" should read -- 50-100 --.

Column 14,
Line 5, "hexaoleate, and" should read -- hexaoleate; and --.

Signed and Sealed this

Eighteenth Day of February, 2003

JAMES E. ROGAN
*Director of the United States Patent and Trademark Office*